United States Patent [19]

Shin et al.

[11] Patent Number: 5,268,017

[45] Date of Patent: * Dec. 7, 1993

[54] METHODS AND COMPOSITIONS FOR TREATING PLANTS EXPOSED TO OZONE

[75] Inventors: Charles C. Shin; Nicolai A. Favstritsky, both of Lafayette, Ind.

[73] Assignee: Great Lakes Chemical Corporation, West Lafayette, Ind.

[*] Notice: The portion of the term of this patent subsequent to Mar. 2, 2009 has been disclaimed.

[21] Appl. No.: 844,242

[22] Filed: Mar. 2, 1992

[51] Int. Cl.$^5$ .............................................. A01N 43/08
[52] U.S. Cl. ............................. 504/294; 71/DIG. 1; 504/140
[58] Field of Search ............................................ 71/88

[56] References Cited

U.S. PATENT DOCUMENTS 4,886,543 12/1989 Shin et al. ................. 71/88

Primary Examiner—Glennon H. Hollrah
Assistant Examiner—B. Bembenick
Attorney, Agent, or Firm—Woodard, Emhardt, Naughton, Moriarty & McNett

[57] ABSTRACT

Methods and compositions for the protection of plant tissue from damage upon exposure to air pollutants, and to assist plant tissue in recovering from air pollution injury, include the application of an effective amount of stress-protectant compositions selected from the group consisting of tetrahydrofurfuryl alcohol, tetrahydrofurfuryl amine and mixtures thereof. The compositions are applied as aqueous solutions containing between about 0.005 and about 25 wt % of the stress-protectant components. Surfactants may be included to improve application of the compositions to the plants.

23 Claims, No Drawings

METHODS AND COMPOSITIONS FOR TREATING PLANTS EXPOSED TO OZONE

BACKGROUND OF THE INVENTION

1. Field of the Invention

The present invention relates to methods and compositions for the treatment of plants to reduce injury due to exposure to polluted air, and more particularly to the application of compositions to plants to minimize or prevent air pollution stress injuries. The present invention further relates to the treatment of plants which have been subjected to injury due to exposure to air pollutants.

2. Description of the Prior Art

Plants are subject to exposure to a variety of external stresses. Air pollution, for example, can significantly affect the growth of plants. It is desirable to treat plants to avoid or reduce any detrimental effects that would otherwise result.

In sufficient concentrations, air pollutants injure plant foliage, significantly alter growth and yield, and thereby can change the quality of marketable plant products. For example, exposure to ozone in concentrations of 0.05 to 0.12 ppm (by volume) for 2 to 4 hours injures leaves of the most sensitive cultivars. During the summer months, the atmosphere over some areas of the U.S. contains levels of ozone ranging from 0.05 to 0.10 ppm (by volume). As reported by the National Loss Assessment Network, crops such as beans, soybeans, peanuts, tobacco, and cotton suffer significant yield losses at these ozone concentrations. Ozone affects vegetation throughout the United States, impairing crops, native vegetation, and the ecosystem more than any other air pollutant.

In addition to ozone, major air pollutants damaging to crops include: peroxyacetyl nitrate, oxides of nitrogen, sulfur oxide, fluoride, agricultural chemicals, and ethylene and other hydrocarbons. Ozone and sulfur dioxide account for 90% of crop damage caused by air-borne pollutants. However, the additional pollutants listed, as well as others, also contribute to crop damage and losses. It has been estimated that American farmers lose $3 billion a year in damaged crops due to air pollution alone.

Although there are chemicals which have been reported to reduce injury to plants due to air pollution, none yet has been of practical utility. For example, scientists reported in 1986 that the injection of ethylene diurea (EDU) into the stem of shade trees could protect the trees from ozone damage. EDU was also determined to be a growth regulator. Test results at that time indicated that EDU altered enzyme and membrane activity within the leaf cell where the photosynthesis of the plant takes place. Under the laboratory conditions, a single soil drench of the EDU was effective in providing protection against acute exposure to ozone. However, the efficacy of the compound for field application has not been established.

In order to be practically useful, a chemical composition must be non-toxic to the plants, environmentally acceptable and relatively inexpensive. The present invention satisfies these requirements and provides for the protection of plants from ozone and other forms of air pollution stresses.

SUMMARY OF THE INVENTION

In accordance with this invention, there are provided methods and compositions for protecting plants and plant products from air pollution stresses, and for promoting recovery of plants from stress injuries. A plant anti-stress chemical composition has been discovered which comprises an aqueous solution containing an effective amount of a chemical component selected from the group of tetrahydrofurfuryl alcohol, tetrahydrofurfuryl amine, and mixtures thereof. The solution is applied to the plant surfaces and tissues prior to and/or after exposure to the air pollutants. The solution preferably includes between about 0.005 and about 25 wt. % of the stress protectant.

Among the objects of this invention is the provision of compositions and methods to protect plants from stress damage due to air pollutants, thereby minimizing crop loss. Another object is the provision of an effective method for treating plants injured due to exposure to air pollutants.

A further object of this invention is to provide air pollution stress protectant compositions and methods which are relatively inexpensive, non-toxic and environmentally acceptable.

These and other objects are features of this invention will be apparent from the description hereafter.

DESCRIPTION OF THE PREFERRED EMBODIMENTS

For the purposes of promoting an understanding of the principles of the invention, reference will now be made to the preferred embodiment of the invention and specific language will be used to describe the same. It will nevertheless be understood that modifications and further applications of the principles of the invention are contemplated as would normally occur to one skilled in the art to which the invention relates.

Exposure of plants to a variety of environmental stresses can result in serious damage. Air pollution, for example, can detrimentally affect the growth of plants. The present invention provides effective, ecologically safe and relatively inexpensive compositions and methods for treating plants subject to exposure to air pollutants.

Injury from air pollutants has characteristic manifestations in plants and is distinguishable from other forms of injury. By way of example, the response of bean plants to ozone exposure has been well defined. When a bean plant is exposed to ozone, an injury begins as a necrotic stippling. As the injury progresses, the foliage develops a bronze appearance on most beans. The degree of injury is revealed in terms of the area of the leaves which becomes bronzed. The present invention is focused on dealing with such air pollution stresses, and is not directed to other forms of plant stress such as that resulting from exposure to chilling or freezing temperatures.

Among the environmental stresses, exposure to air pollutants is of particular concern. As used herein, the term "air pollutants" refers to chemical agents at concentrations in the air which cause or potentially cause damage to plants and/or plant tissues. The term "polluted air" refers to air containing detrimental levels of pollutants. Air pollutants which may adversely affect plants include those discussed in the prior art, such as peroxyacetyl nitrate, oxides of nitrogen, sulfur oxide, fluorides, agricultural chemicals, ethylene and other hydrocarbons, and ozone. The present invention provides compositions and methods which reduce injuries due to air pollutants and/or assist plants in recovering from such injuries.

The extent and nature of damage resulting from exposure to polluted air is exemplified by the effects of ozone on plants. At detrimental levels of ozone in the air, injury to plants leads to leaf chlorosis or necrosis, decreased photosynthetic activity, altered metabolite pools, change in enzyme activity and effects on membrane permeability. Ozone and oxidative stress often lead to damage of membrane lipids, at least partly via lipid peroxidation. Ozone stress is an appropriate and useful model for demonstrating the efficacy of compositions and methods on the protection of plants from air pollution. The present invention provides compositions and methods which can reduce injuries of plants due to Polluted air, especially due to ozone.

In accordance with this invention, a plant stress-protectant composition has been discovered which comprises an aqueous solution containing a stress-protectant component selected from the group consisting of tetrahydrofurfuryl alcohol, tetrahydrofurfuryl amine, and mixtures thereof Preferably, the composition comprises an aqueous solution comprising between about 0.005 and about 25 wt. percent of the stress-protectant component, and most preferably comprises between about 0.05 and about 5 wt. percent of the stress-protectant component. It has also been discovered that the plant stress-protectant composition is effective in promoting a recovery of plants from air pollution stresses.

Tetrahydrofurfuryl alcohol is a colorless, high boiling, primary alcohol having the following structure:

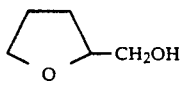

Tetrahydrofurfuryl amine is a colorless, high boiling, primary amine having the following structure:

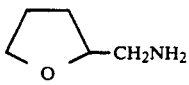

Both tetrahydrofurfuryl alcohol and tetrahydrofurfuryl amine exhibit stress-protectant properties as against exposure to air pollutants. However, tetrahydrofurfuryl alcohol is preferred in accordance with the present invention.

Tetrahydrofurfuryl alcohol (THFA) is produced by the hydrogenation of furfuryl alcohol. As expected on the basis of its structure, tetrahydrofurfuryl alcohol exhibits behavioral characteristics of both alcohol and ethers. Due to its cyclic ether structure, tetrahydrofurfuryl alcohol possesses distinctly unique solvent properties which are desirable. THFA is low in volatility (vapor pressure is 2.3 mm Hg at 39° C), non-damaging and non-toxic, biodegradable, easily absorbable, able to penetrate membranes, considerably soluble in water, in addition to forming multiple hydrogen bonds, and able to dissolve electrolytes. Tetrahydrofurfuryl amine has similarly useful characteristics.

The resistance of plants and plant tissues to air pollution stresses is increased through the application of the stress-protectant compositions of this invention, such as by spraying. The composition is applied at moderate, ambient temperatures, i.e., at temperatures of the air surrounding the plant or plant tissues above a chilling temperature. For spraying, any suitable plant spray apparatus suitable for aqueous solutions may be employed. The plants to be treated are thoroughly sprayed so that all of the plant tissue surfaces are substantially covered. Due to the size, shape and/or other characteristics (such as surface properties) of a plant, an application may require two or more sprayings.

The compositions may be formulated and supplied to the user ready to apply, or in concentrated form and diluted to the desired strength prior to application to the plant. No special handling or mixing steps are required. THFA and tetrahydrofurfuryl amine are stable in aqueous solution. Moreover, these compositions are stable to light and do not need to be stored in an opaque container nor prepared immediately prior to application.

Since aqueous THFA or tetrahydrofurfuryl amine solutions, or mixtures thereof, may not completely wet the leaves of some plants, such as those having waxy surfaces, it is preferred for some applications that the compositions include non-ionic surfactants. Suitable surfactants operate as penetrating agents and otherwise may be inert, or at least non-interfering, components. For example, two different surfactants, polyoxyethylene sorbitan monolaurate (Tween 20) and polyoxyethylene sorbitan monooleate (Tween 80) have been found to improve the effectiveness of the compositions in appropriate circumstances. When non-ionic surfactants are used, it is preferred that the stress-protectant composition contain between about 0.005 and about 0.5 wt. percent of the non-ionic surfactant.

Although the stress-protectant compositions of the present invention may be applied to the plants from immediately prior to 24 hours prior to exposure to the air pollution stress conditions, it is preferred that the composition be applied periodically about every week during the season when the stress level of air pollutant is high. Moreover, for optimal results it is preferred that the stress-protectant compositions be repeatedly applied prior to exposure to the stress level of air pollutants. For additional protection, the stress-protectant compositions may be applied immediately after the stress exposure to help plants or plant products recover from any stress injuries that are incurred. For maximum protection during extended periods of exposure to stress conditions, it may be desirable to apply the stress-protectant compositions periodically, such as weekly.

The following examples serve to further illustrate the invention, with all percentages being by weight unless otherwise indicated. It will be appreciated that these examples are demonstrative only, and the applicability of the compositions and methods described therein extends to the various other plants and plant products, as well as the differing types of air pollution stresses, elsewhere described herein.

EXAMPLE 1

The efficacy of the present invention is readily demonstrated by the results of experiments showing reduction in ozone-induced plant injuries. For this purpose, an ozone sensitive bean plant, c.v. Oregon 91, was used to test the effectiveness of the antipollution agents. For the first study, the pollution stress protectant comprised solutions of differing weight percentages of tetrahydrofurfuryl alcohol in water.

Bean seeds were planted in 6" diameter plastic pots containing a mixture of peat, perlite and vermiculite. The plants were germinated and grown in a clean air greenhouse. The incoming air in the greenhouse was filtered with activated charcoal to make sure that the plants would grow in an environment absolutely free of ozone contamination. When the third trifoliate leaves were developed on the bean plants (25 days old), 20 uniform plants, divided into sets of four, were selected for the test.

Each set of four plants was treated by spraying with various concentrations of THFA solution. The control plants were treated with deionized water. Twenty-four hours after the treatment, the plants were moved to an ozone fumigation chamber. The plants were fumigated with 0.15 ppm ozone for 5.3 hours.

Two days after the ozone fumigation, the exposed plants were assessed visually for injury to two primary and two trifoliate leaves. The visible injury was estimated in terms of area on a 0 to 100% scale, in 5% increments. The injury percents in Table 1 show that the chemical treatment significantly reduced the injury to the plants.

TABLE 1

| Concentration (%) | Primary Leaf #1 | Primary Leaf #2 | Trifoliate Leaf #1 | Trifoliate Leaf #2 | Average Injury % |
|---|---|---|---|---|---|
| 0.00 | 13 | 15 | 84 | 51 | 40 |
| 0.05 | 21 | 13 | 79 | 54 | 42 |
| 0.20 | 5 | 13 | 64 | 48 | 32 |
| 0.50 | 13 | 20 | 64 | 49 | 36 |
| 1.00 | 10 | 8 | 40 | 34 | 23 |

EXAMPLE 2

The same experimental procedure detailed in Example 1 was followed in this test. Twenty-one uniform plants (26 days old), divided into seven sets of three, were selected for the test. Each of the three plants in a set was treated with a given concentration of the stress protectant.

Twenty-four hours after the treatment, the plants were moved to an ozone fumigation chamber. The plants were fumigated with 0.15 ppm ozone for 5 hours. Four days after the ozone fumigation, the injury to each of the exposed plants was assessed visually. The average injury percentages in Table 2 show that treated plants had a substantially lower injury rate than the untreated plants. The effectiveness improved as the concentration of the anti-pollution agent was increased.

TABLE 2

| Concentration (%) | Primary Leaf #1 | Primary Leaf #2 | Trifoliate Leaf #1 | Trifoliate Leaf #2 | Average Injury % |
|---|---|---|---|---|---|
| 0.00 | 27 | 27 | 8 | 30 | 23 |
| 0.05 | 18 | 17 | 7 | 13 | 14 |
| 0.20 | 2 | 8 | 2 | 7 | 5 |
| 0.50 | 12 | 13 | 3 | 7 | 9 |
| 1.00 | 3 | 3 | 3 | 0 | 3 |
| 2.00 | 5 | 0 | 2 | 7 | 3 |
| 4.00 | 2 | 0 | 3 | 5 | 2.5 |

EXAMPLE 3

In this test, all the plants tested were fumigated twice. After the results in Example 2 were tabulated, the same 21 bean plants used in Example 2 were fumigated a second time at the rate of 0.15 ppm ozone for 6 hours. Three days after the second fumigation, the plants were evaluated and data was taken. The treated plants had a much lower injury percent than the non-treated plants. The results in Table 3 show that effectiveness generally increased as the concentration of the antipollution agent was increased.

TABLE 3

| Concentration (%) | Primary Leaf #1 | Primary Leaf #2 | Trifoliate Leaf #1 | Trifoliate Leaf #2 | Average Injury % |
|---|---|---|---|---|---|
| 0.00 | 32 | 27 | 25 | 57 | 35 |
| 0.05 | 23 | 25 | 18 | 27 | 23 |
| 0.20 | 10 | 23 | 17 | 18 | 17 |
| 0.50 | 15 | 23 | 22 | 25 | 22 |
| 1.00 | 18 | 13 | 20 | 18 | 18 |
| 2.00 | 5 | 10 | 22 | 22 | 15 |
| 4.00 | 8 | 15 | 25 | 25 | 17 |

EXAMPLE 4

The same experimental procedure detailed in Example 1 was followed in this test. Eighteen uniform plants were selected and treated. Plants were fumigated at a rate of 0.15 ppm ozone for 6 hours. After 5 days, the plants were assessed to determine the injury to exposed plants and the results are listed in Table 4, showing good efficacy of the treatments. For example, the average injury percentage of the treated plants at 2% of the anti-pollution agent treatment was 10%, compared with 26% for the untreated control plants.

TABLE 4

| Concentration (%) | Primary Leaf #1 | Primary Leaf #2 | Trifoliate Leaf #1 | Trifoliate Leaf #2 | Average Injury % |
|---|---|---|---|---|---|
| 0.00 | 12 | 10 | 43 | 38 | 26 |
| 0.05 | 7 | 5 | 28 | 27 | 16 |
| 0.20 | 7 | 8 | 32 | 27 | 18 |
| 0.50 | 5 | 5 | 27 | 27 | 16 |
| 1.00 | 5 | 5 | 27 | 28 | 16 |
| 2.00 | 5 | 2 | 18 | 13 | 10 |

EXAMPLE 5

The foregoing procedures are repeated for other stress-protectant compositions of the present invention. For example, the anti-stress agents include:

1. tetrahydrofurfuryl alcohol dissolved in deionized (DI) water to make 0.05% and 0.5% THFA aqueous solutions;

2. 0.12 parts of a surfactant, polyoxyethylene sorbitan monolaurate (Tween 20), and 0.05–0.5 parts tetrahydrofurfuryl alcohol dissolved in 99.38–99.83 parts DI water to make an aqueous 0.05–0.5% THFA +0.12% Tween 20 solution;

3. tetrahydrofurfuryl amine dissolved in DI water to make 0.3% tetrahydrofurfuryl amine aqueous solution; and 4. 0.12 parts of a surfactant, Tween 20, and 0.3 parts of tetrahydrofurfuryl amine dissolved in 99.58 parts of DI water to make an aqueous 0.3% tetrahydrofurfuryl amine +0.12% Tween 20 solution.

Application of the foregoing compositions to the plants prior to exposure to polluted air, e.g. ozone-containing air, Provides protection against air pollution injuries. The treated plants display better growth than the untreated plants. Protection of the plants is also obtained upon treatment with aqueous solutions containing as low as 0.005 wt. % and as high as 25 wt. % of the tetrahydrofurfuryl amine, as well as mixtures of the alcohol and the amine yielding total weight percentages as indicated. Generally, treatments with the amine and mixtures of the amine and the alcohol give comparable results to treatments with the tetrahydrofurfuryl alcohol solutions alone. Treatment with Tween-20 alone has no effect on protecting plants from air pollution injury.

EXAMPLE 6

Treatment with the inventive compositions of plants which have already received stress injuries can also contribute to plant recovery and improved plant growth. Plants, injured from air pollution exposure, which are treated immediately following exposure to the injurious stresses, display better growth and development than untreated plants.

While the invention has been described in detail in the foregoing description and its specific Examples, the same is to be considered as illustrative and not restrictive in character. Only the preferred embodiments have been described, and all changes and modifications that come within the spirit of the invention are desired to be protected.

What is claimed is:

1. A method for increasing the resistance of plant tissue to damage upon exposure to ozone thereby reducing damage to plant tissue upon exposure to ozone which comprises applying to the plant tissue an effective amount of an ozone stress-protectant composition selected from the group consisting of tetrahydrofurfuryl alcohol, tetrahydrofurfuryl amine and mixtures thereof.

2. The method of claim 1 in which said applying comprises applying an aqueous solution of the stress-protectant composition.

3. The method of claim 2 in which the aqueous solution contains between 0.005 and 25 wt % of the stress-protectant composition.

4. The method of claim 3 in which the aqueous solution contains between 0.05 and 5.0 wt% of the stress-protectant composition.

5. The method of claim 2 in which the stress-protectant composition consists essentially of an aqueous solution of tetrahydrofurfuryl alcohol.

6. The method of claim 5 in which the aqueous solution contains between 0.05 and 5.0 wt % of the tetrahydrofurfuryl alcohol.

7. The method of claim 2 in which the aqueous solution further contains a non-ionic surfactant.

8. The method of claim 7 in which the aqueous solution contains between 0.05 and 0.5 wt % of the non-ionic surfactant.

9. The method of claim 7 in which the non-ionic surfactant is selected from the group consisting of polyoxyethylene sorbitan monolaurate and polyoxyethylene sorbitan monooleate.

10. The method of claim 1 in which said stress-protectant composition is applied a sufficient time prior to exposure to the stress to permit at least partial absorption of the composition by the plant tissue.

11. The method of claim 10 in which the stress-protectant composition is applied at least about 4 hours prior to exposure of the plant tissue to the stress.

12. The method of claim 10 in which the stress-protectant composition is applied at least about 12 hours prior to exposure of the plant tissue to the stress.

13. The method of claim 10 in which the stress-protectant composition is applied to the plant tissue at least twice prior to exposure of the plant tissue to the stress.

14. The method of claim 11 in which the stress-protectant composition is also applied to the plant tissue after exposure of the plant tissue to the stress.

15. A method for the treatment of plant tissue injured due to exposure to ozone which comprises applying to the plant tissue an effective amount of an ozone stress-recovery composition selected from the group consisting of tetrahydrofurfuryl alcohol, tetrahydrofurfuryl amine and mixtures thereof.

16. The method of claim 15 in which said applying comprises applying an aqueous solution of the stress-recovery composition.

17. The method of claim 16 in which the aqueous solution contains between 0.005 and 25 wt % of the stress-recovery composition.

18. The method of claim 17 in which the aqueous solution contains between 0.05 and 5.0 wt % of the stress-recovery composition.

19. The method of claim 18 in which the stress-recovery composition consists essentially of an aqueous solution of tetrahydrofurfuryl alcohol.

20. The method of claim 19 in which the aqueous solution contains between 0.05 and 5.0 wt % of the tetrahydrofurfuryl alcohol.

21. The method of claim 16 in which the aqueous solution further contains a non-ionic surfactant.

22. The method of claim 21 in which the aqueous solution contains between 0.05 and 0.5 wt % of the non-ionic surfactant.

23. The method of claim 21 in which the non-ionic surfactant is selected from the group consisting of polyoxyethylene sorbitan monolaurate and polyoxyethylene sorbitan monooleate.

* * * * *